US009447466B2

(12) United States Patent
Mutoh et al.

(10) Patent No.: US 9,447,466 B2
(45) Date of Patent: Sep. 20, 2016

(54) METHOD FOR DETERMINATION OR EVALUATION OF TEST SUBSTANCE (75) Inventors: Tatsuro Mutoh, Toyoake (JP); Yu Fukuda, Osaka (JP)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 337 days.

(21) Appl. No.: 13/806,979

(22) PCT Filed: Jun. 23, 2011

(86) PCT No.: PCT/JP2011/064342
§ 371 (c)(1),
(2), (4) Date: Dec. 26, 2012

(87) PCT Pub. No.: WO2011/162317
PCT Pub. Date: Dec. 29, 2011

(65) Prior Publication Data
US 2013/0122512 A1 May 16, 2013

(30) Foreign Application Priority Data
Jun. 25, 2010 (JP) ................. 2010-145494

(51) Int. Cl.
C12Q 1/68 (2006.01)
G01N 33/50 (2006.01)
G01N 33/68 (2006.01)

(52) U.S. Cl.
CPC ......... *C12Q 1/6876* (2013.01); *G01N 33/5023* (2013.01); *G01N 33/5041* (2013.01); *G01N 33/6854* (2013.01); *G01N 2333/07* (2013.01)

(58) Field of Classification Search
None
See application file for complete search history.

(56) References Cited

U.S. PATENT DOCUMENTS

| 5,013,558 | A | 5/1991 | Konishi |
| 5,560,935 | A | 10/1996 | Konishi et al. |
| 6,051,613 | A | 4/2000 | Ohno et al. |
| 6,165,515 | A | 12/2000 | Matsuyama et al. |
| 7,923,254 | B2 | 4/2011 | Nishioka et al. |
| 2002/0137893 | A1 | 9/2002 | Burton et al. |
| 2006/0051376 | A1 | 3/2006 | Nishioka |
| 2006/0051835 | A1 | 3/2006 | Takahashi et al. |
| 2006/0263388 | A1 | 11/2006 | Nishioka |
| 2007/0218037 | A1 | 9/2007 | Nishioka |
| 2009/0272649 | A1 | 11/2009 | Nishioka et al. |
| 2010/0048408 | A1 | 2/2010 | Naiki et al. |
| 2011/0111051 | A1 | 5/2011 | Oishi et al. |

FOREIGN PATENT DOCUMENTS

| EP | 0 916 344 A2 | 5/1999 |
| JP | A-53-101515 | 9/1978 |
| JP | A-55-87724 | 7/1980 |
| JP | A-1-265028 | 10/1989 |
| JP | A-1-319422 | 12/1989 |
| JP | A-2-28119 | 1/1990 |
| JP | A-7-97336 | 4/1995 |
| JP | A-8-291077 | 11/1996 |
| JP | A-10-194978 | 7/1998 |
| JP | A-11-80005 | 3/1999 |
| JP | A-11-139977 | 5/1999 |
| JP | A-2000-16942 | 1/2000 |
| JP | A-2000-336034 | 12/2000 |
| JP | A-2003-18992 | 1/2003 |
| JP | A-2004-300146 | 10/2004 |
| JP | A-2009-40786 | 2/2009 |
| WO | WO 2004/039383 A1 | 5/2004 |
| WO | WO 2008/029836 A1 | 3/2008 |
| WO | WO 2008/029838 A1 | 3/2008 |
| WO | WO 2009/028605 A1 | 3/2009 |

OTHER PUBLICATIONS

Hata et al. (Japan J Pharmacol 48: 479-490, 1988).*
Yoshida et al. (J Neurosurg Spine 9: 411-418, 2008).*
Purmessur et al (Arthritis Res Ther 10: R99(1-9), 2008).*
Yoneda, (2000, pp. 1-19) English translation of Japanese publication cited as Cite No. 34 in IDS dated Feb. 18, 2015.*
Kurihara et al (J Periodontol 74: 76-84, 2003—abstract only).*
Givalois et al (Endocrinol 145: 4737-4747, 2004).*
Loh et al (Exp Neurol 170: 72-84, 2001).*
Hoshino, Y. et al., "Neurotropin Demonstrates Cytoprotective Effects in Lung Cells through the Induction of Thioredoxin-1," *American Journal of Respiratory Cell and Molecular Biology*, 2007, pp. 438-446, vol. 37, No. 4.
Mori, H. et al., "Effect of a Non-Protein Fraction from an Extract of the Inflamed Skin of Rabbits Inoculated with *Vaccinia* Virus (Neurotropin) on Meth A-Induced Delayed Type Hypersensitivity," *Japanese Journal of Pharmacology*, 1990, pp. 468-472, vol. 54, No. 4.
Morita, S. et al., "Differential Action of Nerve Growth Factor, Cyclic AMP and Neurotropin on PC12h Cells," *Cell Structure and Function*, 1988, pp. 227-234, vol. 13, No. 3.
Nakamura, K. et al., "Action of Neuroptropin on Rat Hypothalamic Neurons in Tissue Slices," *Brain Research Bulletin*, 1990, pp. 811-817, vol. 24, No. 6.
Extended European Search Report issued in European Patent Application No. 11798198.5 on Sep. 23, 2013.

(Continued)

Primary Examiner — Daniel E Kolker
Assistant Examiner — Aditi Dutt
(74) Attorney, Agent, or Firm — Oliff PLC (57) ABSTRACT An object of the present invention is to provide a method for determination or evaluation of an extract from inflamed tissues inoculated with vaccinia virus where the enhancement of activation of neurotrophic factor such as BDNF in cultured cells or the enhancement of activation of proteins participating therein is used as an indicator. The present invention relates to a novel method for determination or evaluation of an extract from inflamed tissues inoculated with vaccinia virus and relates to a method for determination or evaluation of the extract where the enhancement of production of neurotrophic factor such as BDNF in cultured cells or the enhancement of activation of various proteins in intracellular signaling pathway participating in production of BDNF, etc. is used as an indicator.

7 Claims, 5 Drawing Sheets (56) References Cited

OTHER PUBLICATIONS

Yoneda, "Sekizui Shono Henseisho ni Taisuru Tekiogai Shiyo Iyakuhin 'Vaccinia Virus Sesshu Kato Ensho Hifu Chushutsueki Seizai (Neurotropin)' no Kaihatsu Kenkyu ( Japan Health Sciences Foundation S)" Soyaku To Human Science Sogo Kenkyu Jigyo Juten Kenkyu Hokoku Heisei 11 Nendo Dai 4 Bun'ya Kisho Shippei Chiryoyaku To no Kaihatsu ni Kansuru Kenkyu, 2000, pp. 36-42.

Ginty et al., "Nerve Growth Factor Activates a Ras-Dependent Protein Kinase That Stimulates c-fos Transcription via Phosphorylation of CREB," *Cell*, vol. 77, Jun. 3, 1994, pp. 713-725.

Castren, "Is Mood Chemistry?" *Nature Reviews Neuroscience*, vol. 6, Mar. 2005, pp. 241-246.

Ichiki, "Critical Role of cAMP Response Element Binding Protein in the Signaling of Angiotension II and Tumor Necrosis Factor α,"*The Journal of Japanese College of Angiology*, vol. 47, No. 4, Sep. 12, 2007, pp. 377-381.

Fukuda et al., "Stimulated Neuronal Expression of Brain-Derived Neurotropic Factor by Neurotropin," *Molecular and Cellular Neuroscience*, vol. 45, 2010, pp. 226-233.

Muto et al., "Chintsuyaku Neurotropin wa Shinkei BDNF Hatsugen o Sokushin suru," *Societas Neurologica Japonica Gakujutsu Taikai Program Shorokushu*, vol. $52^{nd}$, 2011, p. 476.

Sep. 20, 2011 International Search Report issued in International Patent Application No. PCT/JP2011/064342.

Chen et al., "The Signaling Pathway of Nerve Growth Factor Inducing Survival and Differentiation of Neurons and its Relationship with Asthma," Progress of Anatomical Sciences vol. 13, No. 4, pp. 388-391, 2007.

\* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
tggacaaccc tttcgagttc                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
cgtccacatt tgttgagcac                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
ccgagattgg agcctaacag                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tgcaggttgc tgtttttcag                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
atcactgcca cccagaagac                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tttctagacg gcaggtcagg                    20

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 7
gctgcaaaca tgtccatgag                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
atgggattgc acttggtctc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
gcttcccttg atctgactgg                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
atgatgctgg gaacaggaag                                                20
```

METHOD FOR DETERMINATION OR EVALUATION OF TEST SUBSTANCE

TECHNICAL FIELD

The present invention relates to a novel method for determination, evaluation, etc. of an extract from inflamed tissues inoculated with vaccinia virus and, more particularly, it relates to a method for determination or evaluation of the test substance (which is an extract from inflamed tissues inoculated with vaccinia virus) where an action of the test substance to BDNF expression in cultured cells or an action thereof to various proteins in intracellular signaling pathway is used as an indicator. The term reading "treatment" in the context as such means to culture the cells in the presence of the substance (Hereinafter, the term has the same meaning).

BACKGROUND ART

Brain-derived neurotrophic factor (BDNF) belongs to a neurotrophin family together with nerve growth factor (NGF) and neurotrophin-3 (NT-3) and is a secretory protein produced in various cells such as nerve cell (neuron), glia cell (microglia, stellate cell, oligodendroglia, etc.), etc. BDNF is unevenly distributed in central nerve system centering on hippocampus and has been known to exhibit various physiological activities in nerve system such as existence and maintenance of nerve cells, adjustment of shape of neurite, adjustment of function of synapse, control of nerve reversibility, etc.

It has been known that BDNF expression in vivo is finally controlled by activation (phosphorylation) of a CREB (cAMP-response-element-binding protein) via intracellular signaling pathway called an MAP kinase (mitogen-activated protein kinase or MARK which is a protein activating the mitogenic factor)/CREB pathway being initiated by activation of TrkB (tropomyosin receptor kinase B) which is a highly affinitive receptor to BDNF. Thus, it has been said that, when BDNF binds to TrkB on cell surfaces so that TrkB is activated, there are induced CREB activation by an MEK (MAPK kinase or MAP kinase kinase)/ERK (extracellular-signal-regulated kinase) pathway and CREB activation by a PI3K (phosphoinositide 3-kinase)/Akt pathway (in the present application, both pathways are called MAP kinase/CREB pathway).

With regard to the MEK/ERK pathway, it has been said that, from activation of a Trk receptor, activation of various proteins such as Grb2/Sos, Ras, Raf, MEK1/2, ERK1/2, Rsk, etc. is successively transmitted and, finally, CREB is activated (phosphorylated) to express BDNF, etc. With regard to a PI3K/Akt pathway, it has been said that, due to activation of a Trk receptor, activation of proteins such as PI3K, Akt, P38MAPK, etc. is successively transmitted whereby phosphorylation of CREB is induced similarly.

The present inventors have found that an extract from inflamed tissues inoculated with vaccinia virus has an action to the expression of neurotrophic factor such as BDNF in cultured cells. They have further clarified that, during that time, the extract acts on various proteins in intracellular signaling pathway participating in the expression of BDNF, etc. and that those actions are suppressed by each of inhibitors to Trk receptor, PI3K, P38PAPK, MEK1/2, etc. The method of determination or evaluation according to the present invention is based on the study results as such.

The extract from inflamed tissues inoculated with vaccinia virus as an active ingredient in the ameliorating or therapeutic agent for chronic prostatitis, interstitial cystitis an/or urination disorders of the present invention (hereinafter referred to as "the medicinal agent of the present invention") is disclosed to have the following effects: an analgesic effect, sedative effect, anti-stress effect and anti-allergic effect (see Patent Document 1); an immunostimulating effect, anti-cancer effect and cirrhosis inhibitory effect (see Patent Document 2); a treatment effect against idiopathic thrombocytopenic purpura (see Patent Document 3); a treatment effect against postherpetic neuralgia, brain edema, dementia, spinocerebellar degeneration and the like (see Patent Document 4); a treatment effect against Raynaud syndrome, diabetic neuropathy, sequelae of subacute myelo-optico-neuropathy and the like (see Patent Document 5); a kallikrein production inhibitory effect and peripheral circulatory disorder improving effect (see Patent Document 6); a bone atrophy improving effect (see Patent Document 7); a nitric oxide production inhibitory effect effective for the treatment of sepsis and endotoxic shock (see Patent Document 8); a treatment effect against osteoporosis (see Patent Document 9); a treatment effect against AIDS based on a Nef action inhibitory effect and chemokine production inhibitory effect (see Patent Documents 10 and 11); a treatment effect against ischemic disorders such as cerebral infarction (see Patent Document 12); a treatment effect against fibromyalgia syndrome (see Patent Document 13); and a treatment effect against infections (see Patent Document 14); prophylactic or alleviating effect for a peripheral nerve disorder induced by an anti-cancer agent (see Patent Document 15) and the like.

However, this is for the first time that the enhancement of BDNF expression by an extract from inflamed tissues inoculated with vaccinia virus and an adjusting action therefore are clarified and it has not been known up to now for a method of determining or evaluating the extract where the enhancement of BDNF expression, the enhancement of activations of various proteins in intracellular signaling pathway participating therein, etc. are used as indicators.

PRIOR ART DOCUMENTS

Patent Documents

Patent Document 1: Japanese Patent Laid-Open No. Sho-53-101515
Patent Document 2: Japanese Patent Laid-Open No. sho-55-87724 (pages 3, 5 and 6)
Patent Document 3: Japanese Patent Laid-Open No. Hei-1-265028 (pages 1 and 2)
Patent Document 4: Japanese Patent Laid-Open No. Hei-1-319422 (pages 3 and 4)
Patent Document 5: Japanese Patent Laid-Open No. Hei-2-28119 (page 3)
Patent Document 6: Japanese Patent Laid-Open No. Hei-7-97336 (page 4)
Patent Document 7: Japanese Patent Laid-Open No. Hei-8-291077
Patent Document 8: Japanese Patent Laid-Open No. Hei-10-194978
Patent Document 9: Japanese Patent Laid-Open No. Hei-11-80005 (pages 2 and 3)
Patent Document 10: Japanese Patent Laid-Open No. Hei-11-139977
Patent Document 11: Japanese Patent Laid-Open No. 2000-336034 (pages 2 and 3)
Patent Document 12: Japanese Patent Laid-Open No. 2000-16942

Patent Document 13: International Publication No. WO 2004/039383

Patent Document 14: Japanese Patent Laid-Open No. 2004-300146

Patent Document 15: International Publication No. WO2009/028605

SUMMARY OF THE INVENTION

Problems to be Solved by the Invention

An object of the present invention is to provide a method for determining or evaluating an extract from inflamed tissues inoculated with vaccinia virus where the expression of a neurotrophic factor such as BDNF in cultured cells or the action to various proteins in intracellular signaling pathway participating therein are used as indicators.

Means for Solving the Problems

The present inventors have conducted extensive studies on pharmacological action of an extract from inflamed tissues inoculated with vaccinia virus and, as a result, they have found that the extract acts on the expression of a neurotrophic factor such as BDNF in cultured cells and acts on various proteins in intracellular signaling pathway participating in the expression of BDNF, etc. and achieved the present invention as a method for determining or evaluating an extract from inflamed tissues inoculated with vaccinia virus using the above as indicators.

Advantages of the Invention

It has been clarified that an extract from inflamed tissues inoculated with vaccinia virus has an action to the expression of a neurotrophic factor such as BDNF in cultured cells and to various proteins in intracellular signaling pathway participating therein. The expression of BDNF, etc. and the action to proteins participating therein can be measured by a simple method. Since an extract from inflamed tissues inoculated with vaccinia virus is a multicomponent substance comprising quite a lot of components, it is very difficult to determine or evaluate its action by means of the amount, etc. of single or plural component(s) contained therein and to guarantee the pharmaceutical effect, etc. With this regard, the method of determination or evaluation of the present invention is very highly useful in such a respect that the action of an extract from inflamed tissues inoculated with vaccinia virus can be easily determined or evaluated thereby and accordingly that the method can be utilized for guaranteeing the pharmaceutical effect of said extract. Incidentally, the term reading "determination or evaluation" in the present application covers all of the concepts where the object is checked and ascertained by means of test, inspection, etc.

MODE FOR CARRYING OUT THE INVENTION

The present invention relates a method of determining or evaluating an extract from inflamed tissues inoculated with vaccinia virus where cultured cells are treated with an extract from inflamed tissues inoculated with vaccinia virus and then the expression of BDNF, etc. or the activation and the like of various proteins in intracellular signaling pathway participating therein is/are measured.

As to the cells which can be used in the present invention, the simplest and most convenient ones are the commercially available cultured cells. One of the most preferred examples thereof is human neuroblastoma SH-SY5Y cells which express BDNF, etc. and TrkB which is a highly affinitive receptor thereof. In the present invention however, not only SH-SY5Y cells but also other cells such as PC12 cells (pheochromocytoma derived from adrenal medulla of rats) or Schwann cells (sciatic nerve of newly-born rats) may be used as well.

The test substance in a method of determination or evaluation according to the present invention is a physiologically active substance (an extract from inflamed tissues inoculated with vaccinia virus) which is produced in inflamed tissues upon inoculation of vaccinia virus to animals and, with regard to a method for extracting said substance from morbid tissues and the pharmacological activity thereof, etc., many papers have been reported already as mentioned above (cf. the above Patent Documents 1 to 15, etc.).

A preparation of an extract from inflamed skins of rabbits inoculated with vaccinia virus is a commercially available pharmaceutical product which is available for the test substance of the present invention. The preparation, as described in pages 2978 to 2980 of "Drugs in Japan, Ethical Drugs" (2010, edited and published by Japan Pharmaceutical Information Center), contains non-proteinous active substances extracted and separated from the inflamed skin tissues of rabbits inoculated with vaccinia virus. The preparation is known to be effective against low back pain, cervicobrachial syndrome, symptomatic neuralgia, periarthritis scapulohumeralis, osteoarthritis, itchiness accompanied with skin diseases (eczema, dermatitis, urticaria), allergic rhinitis, sequelae of subacute myelo-optico-neuropathy such as coldness, paresthesia and pain, postherpetic neuralgia and the like. The preparation is approved as an ethical drug in the form of hypodermic, intramuscular and intravenous injection products and of tablets and is commercially available.

Hereinafter, the process for producing the extract of inflamed tissues inoculated with vaccinia virus as an active ingredient in the test substance of the present invention and the like will be described.

The extract from inflamed tissues inoculated with vaccinia virus of the test substance of the present invention can be obtained by the following manner: inflamed tissues inflamed by the inoculation with vaccinia virus is crushed; an extraction solvent is added; the tissue fragments are removed therefrom; then deproteinization is carried out; the deproteinized solution is adsorbed onto an adsorbent; and then the active ingredient is eluted.

The extract from inflamed tissues inoculated with vaccinia virus is produced, for example, according to the following process.

(a) Inflamed skin tissues of rabbits, mice or the like by the inoculation with vaccinia virus are collected, and the inflamed tissues are crushed. To the crushed tissues an extraction solvent such as water, phenol water, physiological saline or phenol-added glycerin water is added. Then, the mixture is filtered or centrifuged to obtain an extraction liquid (filtrate or supernatant).

(b) The pH of the extraction liquid is adjusted to be acidic and the liquid is heated for deproteinization. Then, the deproteinized solution is adjusted to be alkaline, heated, and then filtered or centrifuged.

(c) The obtained filtrate or supernatant is made acidic and adsorbed onto an adsorbent such as activated carbon or kaolin.

(d) To the adsorbent, an extraction solvent such as water is added, the pH is adjusted to alkaline, and the adsorbed component is eluted to obtain the extract from inflamed tissues inoculated with vaccinia virus. Subsequently, as desired, the eluate may be evaporated to dryness under reduced pressure or freeze-dried to give a dried material.

Each step as mentioned above is further described in detail as follows:

About (a):

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skin tissues of rabbits.

The inflamed tissues are collected and crushed, and 1 to 5 volumes of extraction solvent is added to make an emulsified suspension. As for the extraction solvent, distilled water, physiological saline, weakly acidic to weakly basic buffer and the like can be used, and stabilizers such as glycerin, antibacterial/antiseptic agents such as phenol, and salts such as sodium chloride, potassium chloride or magnesium chloride may be suitably added. At this time, the extraction may be facilitated by breaking the cellular tissues with treatment such as freezing and thawing, ultrasonic waves, cell membrane dissolving enzymes or surfactants.

About (b):

The obtained emulsified extraction liquid is subjected to filtration, centrifugation or the like to remove tissue fragments, and then deproteinized. The deproteinization operation may be carried out by a generally known method, for example, heat treatment, treatment with a protein denaturant such as an acid, base, urea and guanidine, treatment with an organic solvent such as acetone, isoelectric precipitation, and salting out can be applied. Then, by a general method for removing insolubles such as filtration using filter paper (for example, cellulose or nitrocellulose), glass filters, Celite, Seitz filters or the like, ultrafiltration and centrifugation, the precipitated insoluble protein is removed.

About (c):

The extraction liquid containing active ingredients obtained in this manner is acidified, preferably adjusted to pH 3.5 to 5.5 with an acid such as hydrochloric acid, sulfuric acid or hydrobromic acid, and then adsorbed onto an adsorbent. Examples of the usable adsorbent include activated carbon and kaolin. The adsorbent may be added into the extraction liquid to stir, or the extraction liquid may be passed through a column filled with the adsorbent to adsorb the active ingredients onto the adsorbent. When the adsorbent is added into the extraction liquid, the solution is removed by filtration, centrifugation, or the like to obtain the adsorbent in which the active ingredients are adsorbed.

About (d):

In order to elute (desorb) the active ingredients from the adsorbent, an elution solvent is added to the adsorbent to elute at room temperature or with suitable heating or with stirring, and the adsorbent is removed by a general method such as filtration, centrifugation, or the like. As for the elution solvent to be used, a basic solvent such as water, methanol, ethanol or isopropanol that are adjusted to have a basic pH or a suitable mixture thereof may be used, and preferably water adjusted to pH 9 to 12 may be used.

The extract (eluate) obtained in this manner may be properly prepared in a suitable form as a raw material for a formulation or a pharmaceutical formulation. For example, the solution may be adjusted to have nearly neutral pH to be a raw material for a formulation, and may be adjusted to have a desired concentration by concentration or dilution. In addition, for a formulation for injection, sodium chloride may be added to prepare a solution isotonic to physiological saline. Furthermore, the solution may be concentrated to dryness or freeze-dried to prepare a solid form available for the raw material of tablets or the like.

Examples of an administration method to a patient include oral and other administrations such as subcutaneous, intramuscular and intravenous administrations. The dose can be suitably determined depending on the type of extract from inflamed tissues inoculated with vaccinia virus. The dose that is approved in the commercially available preparation according to the "Drugs in Japan, Ethical Drugs" (page 2978) is principally 16 NU per day by oral administration and 3.6 to 7.2 NU per day by injection. However, the dose may be appropriately increased or decreased depending on the type of disease, degree of seriousness, individual difference in the patients, method of administration, period of administration and the like (NU: Neurotropin unit. Neurotropin unit is defined by $ED_{50}$ value of analgesic effect measured by a modified Randall-Selitto method using SART-stressed mice that are chronic stressed animals showing a lowered pain threshold than normal animals. One NU indicates the activity of 1 mg of analgesic ingredients in Neurotropin preparations when the $ED_{50}$ value is 100 mg/kg of the preparation).

As hereunder, specific examples for the manufacture of the extract from inflamed tissues inoculated with vaccinia virus, and the results of the pharmacological tests regarding the enhancement of BDNF expression by the extract, although the present invention is not limited at all by the description of those Examples.

EXAMPLES

Example 1

Skins of healthy adult rabbits were inoculated with vaccinia virus. The inflamed skins were removed and crushed, and to the crushed skins, phenol water was added. Then, the mixture was filtered under pressure, and the obtained filtrate was adjusted to pH 5 with hydrochloric acid, and then heated at 90 to 100° C. for 30 minutes. After deproteinization by filtration, the filtrate was adjusted to pH 9 with sodium hydroxide, further heated at 90 to 100° C. for 15 minutes, and then filtered. The filtrate was adjusted to about pH 4.5 with hydrochloric acid, and 2% activated carbon was added. The mixture was stirred for 2 hours and then centrifuged. To the collected activated carbon, water was added. The mixture was adjusted to pH 10 with sodium hydroxide, stirred at 60° C. for 1.5 hours, and then centrifuged and filtered to obtain a supernatant. To the collected activated carbon, water was added again. The mixture was adjusted to pH 11 with sodium hydroxide, stirred at 60° C. for 1.5 hours, and then centrifuged to obtain a supernatant. The two supernatants were combined and neutralized with hydrochloric acid to obtain an extract from inflamed skins of rabbits inoculated with vaccinia virus.

Example 2

Skins of healthy adult rabbits were inoculated with vaccinia virus to be infected. Subsequently, the inflamed skins were aseptically removed and chopped, and then phenol-added glycerin water was added. The mixture was ground with a homogenizer to be emulsified. Subsequently, the emulsion was filtered. The obtained filtrate was adjusted to weak acidity (pH 4.5 to 5.5) with hydrochloric acid, then heated at 100° C. and filtered. The filtrate was adjusted to weak alkalinity (pH 8.5 to 10.0) with sodium hydroxide, further heated at 100° C. and then filtered. The filtrate was adjusted to about pH 4.5 with hydrochloric acid, and about 1.5% activated carbon was added. The mixture was stirred for 1 to 5 hours and then filtered. To the activated carbon collected by the filtration, water was added. The mixture was adjusted to pH 9.4 to 10 with sodium hydroxide, stirred for 3 to 5 hours, and then filtered. The filtrate was neutralized with hydrochloric acid.

Example 3

Skins of healthy adult rabbits were inoculated with vaccinia virus to be activated. Then the activated skins were aseptically removed and chopped, and water was added. The mixture was ground with a homogenizer to be emulsified. Subsequently, the emulsion was filtered under pressure. The obtained filtrate was adjusted to pH 5.0 with hydrochloric acid, and then heated at 100° C. with flowing steam. After deproteinization by filtration, the filtrate was adjusted to pH 9.1 with sodium hydroxide, further heated at 100° C. and then filtered. The filtrate was adjusted to pH 4.1 with hydrochloric acid, and 2% activated carbon was added. The mixture was stirred for 2 hours and then filtered. To the filtrate, 5.5% activated carbon was further added, and the mixture was stirred for 2 hours and then filtered. To the activated carbon collected by the former filtration, water was added. The mixture was adjusted to pH 9.9 with sodium hydroxide, stirred at 60° C. for 1.5 hours, and then filtered. To the former activated carbon and the latter activated carbon, water was added. The mixture was adjusted to pH 10.9 with sodium hydroxide, stirred at 60° C. for 1.5 hours, and then filtered. The filtrates were combined and neutralized with hydrochloric acid. Then, the filtrate was desalted by electrodialysis using a membrane with a molecular weight of 100, and dried under reduced pressure.

Now there is shown an example of the result of pharmacological test when an extract from inflamed tissues inoculated with vaccinia virus of the present invention prepared in the above Example 1 was used as the test substance and the cultivation of human neuroblastoma SH-SY5Y cells in the presence thereof was conducted. As to the SH-SY5Y cells, there were used such ones being pre-cultured, according to a method of Hamano, et al. (*Molecular Brain Research*, vol. 137, pages 70 to 76, 2005), in a humidified incubator of 37° C. and 5% $CO_2$ in a Dulbecco-modified Eagle medium (Gibco DMEM of Invitrogen) to which 10% fetal bovine serum (FCS), 1 mL of pyruvic acid, 0.37% of glucose and 25 mIU/mL of penicillin/streptomycin were added. It was confirmed that, in each of the cultured cells after treating with the test substance, neither morphological change within 48 hours nor lowering of cell survival rate by a Trypan Blue pigment exclusion test was noted. After completing the test, all data were subjected to statistic analysis according to Student's t-test (SAS System version 8.2, SAS Institute Japan) to conduct the test of significance using 0.05 (5%) and 0.01 (1%) as significance levels.

Pharmacological Test 1: Expression of BDNF with Elapse of Time

Figure 1:
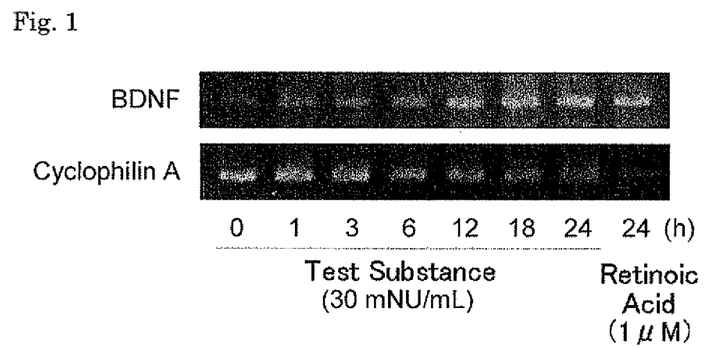
FIG. 1 is an electrophoretic drawing which shows the result where the expression of BDNF (in mRNA levels) when SH-SY5Y cells were treated with a test substance (which is an extract from inflamed tissues inoculated with vaccinia virus prepared by the method of Example 1 and is the same as the "test substance" used in the pharmacological test of the present application) or with retinoic acid was checked with elapse of time.

SH-SY5Y cells ($5 \times 10^5$ cells) were treated with the test substance (30 mNU/mL) or with retinoic acid (1 μM) as a positive control and cultured in a serum-free DMEM (Dulbecco's modified Eagle's medium) for 0, 1, 3, 6, 12, 18 and 24 hour(s). After removing the supernatant liquid of the culture, total RNA was isolated by a TRIzol reagent (Invitrogen) and recovery rate and purity were measured by means of ultraviolet absorptions at 260 nm and 280 nm (GeneQuant Pro, GE Healthcare). RNA equivalent amount was subjected to a reverse transcription to a single stranded DNA using a random primer by a Super Script III First Strand DNA Synthetic Kit (Invitrogen) and then subjected to a semi-quantitative PCR (polymerase chain reaction) by Taq DNA polymerase (Invitrogen). Incidentally, PCR primers (Invitrogen) for BDNF and cyclophilin A (internal standard gene) were designed according to a method of Yamamoto, et al. (*Neurochemical Research*, vol. 21, no. 8, pages 929 to 938, 1996). The PCR product was separated by 3% agarose gel (NuSieve 3:1 agarose, Takara Bio) electrophoresis and bands of BDNF and cyclophilin A were dyed with ethidium bromide (0.1 μg/mL) to visually detect. Linearity of the amount of the product with template in PCR was separately confirmed. An example of the above test result is shown in FIG. 1.

Pharmacological Test 2: Dose-Dependent Expression of Neurotrophic Factors

SH-SY5Y cells (about $5 \times 10^5$ cells) were treated with the test substance (0, 2, 10, 50 and 250 mNU/mL) and cultured in a serum-free DMEM medium for 24 hours. After that, the same as in the above Pharmacological Test 1, the extracted total RNA was subjected to a semi-quantitative PCR and the PCR product was separated by an agarose gel electrophoresis whereupon bands of NGF, BDNF, NT-3, TrkA, TrkB and GAPDH (glyceraldehydes-3-phosphate dehydrogenase) were visually detected. Incidentally, each of PCR primers (Invitrogen) for NGF, BDNF and NT-3 was designed according to a method of Yamamoto, et al. (*Neurochemical Research*, vol. 21, no. 8, pages 929 to 938, 1996) and each of PCR primers (Sigma Ganosys) for TrkA (tropomyosin-related kinase A), TrkB (tropomyosin-related kinase B) and GAPDH was independently designed as the following sequences [TrkA (178 bp): 5'-tggacaaccctttcgagttc-3' 5'-cgtccacatttgttgagcac-3', TrkB (188 bp): 5'-ccgagattggagc-ctaacag-3' 5'-tgcaggttgctgtttttcag-3', GAPDH: 5'-atcactgc-cacccagaagac-3' 5'-tttctagacggcaggtcagg-3'].

Figure 2:
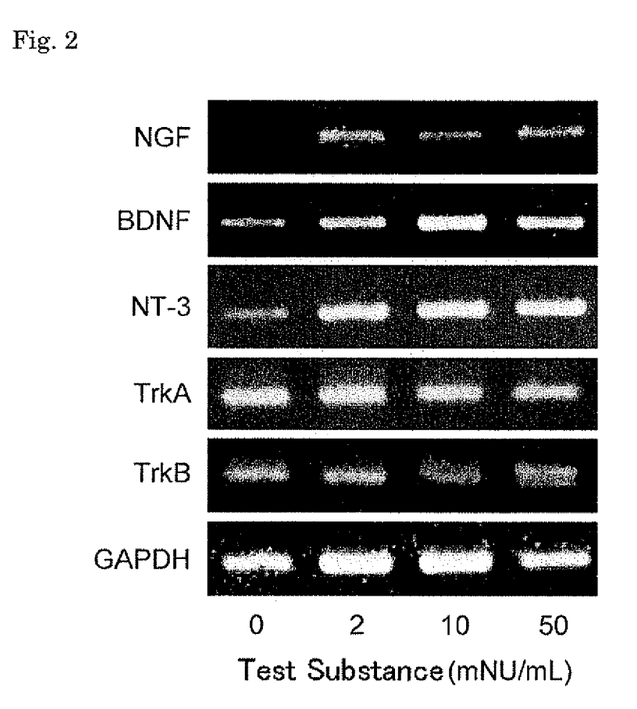
FIG. 2 is an electrophoretic drawing which shows the result where the expression of various neurotrophic factor (in mRNA levels) was checked when SH-SY5Y cells were treated with the test substance.
Figure 3:
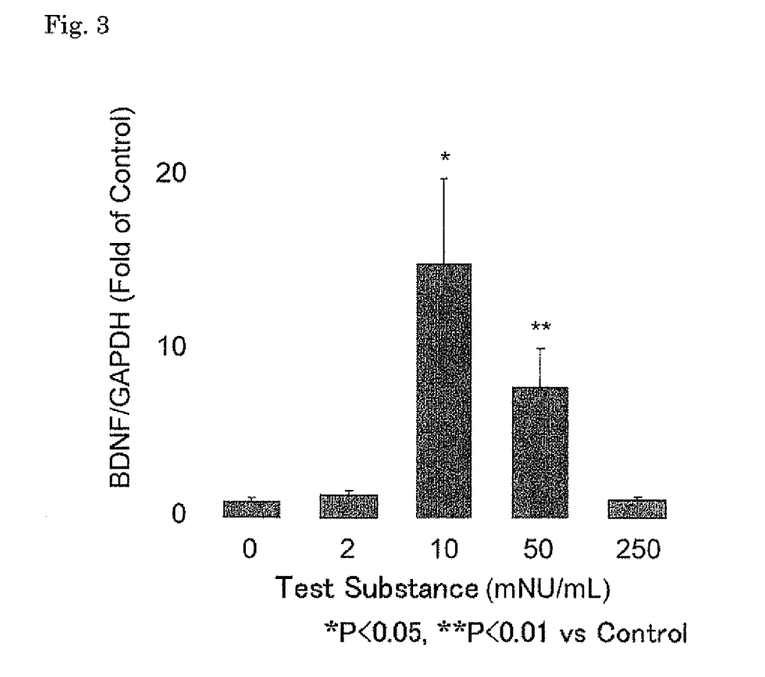
FIG. 3 is an electrophoretic drawing which shows the result where the expression of BDNF (in mRNA levels) was checked when SH-SY5Y cells were treated with the test substance.

Further, with regard to the extracted total RNA, mRNA of BDNF was quantified by a real-time PCR system (Prism 7900 HT, Applied Biosystems) using a template cDNA of an object product where the concentration is already known. Incidentally, the PCR primers for BDNF and GAPDH have the following nucleotide sequences [BDNF: 5'-gctgcaaacat-gtccatgag-3' 5'-atgggattgcacttggtctc-3', GAPDH: 5'-atcact-gccacccagaagac-3' 5'-tttctagacggcaggtcagg-3']. The result is expressed as such a value where a control (treated with physiological saline) was defined as 1.0 after obtaining a mean value for measuring the transcribed copy numbers of BDNF to GAPDH for eight times. An example of the semi-quantitative PCR and an example of the quantitative PCR of the above test are shown in FIG. 2 and FIG. 3, respectively.

Pharmacological Test 3: Expression of Intracellular BDNF

SH-SY5Y cells ($1 \times 10^6$ cells) were cultured for 24 hours in the presence of the test substance (0, 2, 10 and 50 mNU/mL). After that, the SH-SY5Y cells ($1 \times 10^6$ cells) were scraped off from a plate and washed with an ice-cooled phosphate-buffered physiological saline (PBS) and the cell pellets were treated with a cytolyzing buffer containing a mixture of protease inhibitors (Sigma) (20 mM HEPES: 4-(2-hydroxyethyl)-1-piperazineethanesulfonic acid; pH 7.2, 1% Nonidet P-40, 10% glycerol, 50 mM NaF, 1 mM phenylmethylsulfonyl fluoride and 1 mM NaVO$_4$). After removing the residual cell dusts, the cytolyzed product was stored at −80° C. until subjecting to an ELISA (enzyme-linked immuno-solvent assay). Incidentally, the amount of protein in the cytolyzed product was measured by a BCA protein assay kit (Thermo Fisher Scientific).

Figure 4:
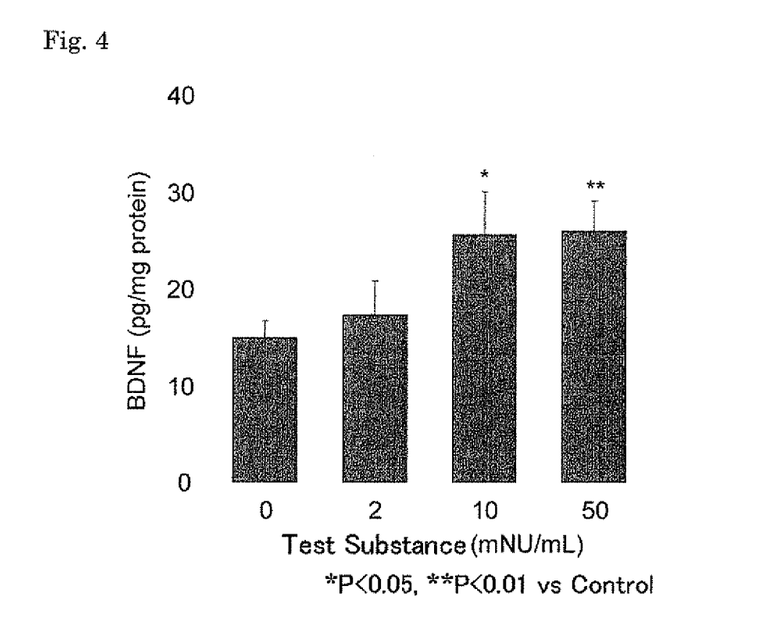
FIG. 4 is an electrophoretic drawing which shows the result where the expression of BDNF (in protein levels) in the cells was checked when SH-SY5Y cells were treated with the test substance.

After that, BDNF in the stored cytolyzed product was quantified according to our standard protocol using a commercially available ELISA kit (Emax ELISA kits, Promega). Thus, the corresponding antibody for capturing the BDNF was bound to the surface of 96-well polystyrene plate (lumulon 4HBX, Thermo Fisher Scientific) and the incorporated BDNF was bound to the secondary antibody and detected by a species-specific antibody labeled with horse-radish peroxidase (HRP). After removing the non-bound labeled antibody, the coloring substrate at 450 nm was measured using a microplate reader (Benchmark microplate reader, BioRad) to calculate the activity of the bound enzyme. Intracellular BDNF within a range of from 3.9 to 500 pg/mL was quantified using those kits. Incidentally, the cross reaction with other neurotrophic factor proteins was less than 2%. The result was shown in terms of mean value of n=3 and standard error. An example of the above test result is shown in FIG. 4.

Pharmacological Test 4: Expression of c-Fos

Figure 5:
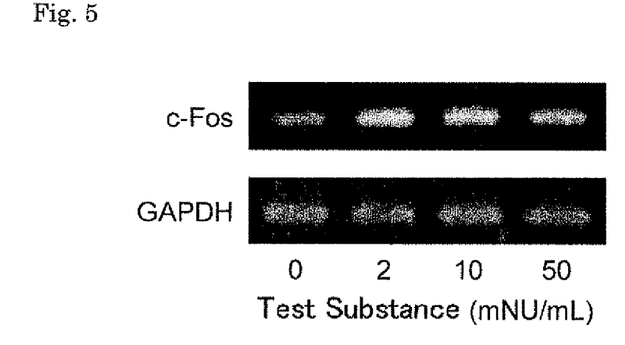
FIG. 5 is an electrophoretic drawing which shows the result where the expression of c-Fos (in mRNA levels) was checked when SH-SY5Y cells were treated with the test substance.

SH-SY5Y cells ($5 \times 10^5$ cells) were cultured for 24 hours with the test substance (0, 2, 10 and 50 mNU/mL). After that, the same as in the above Pharmacological Test 1, the isolated RNA was subjected to a semi-quantitative RT-PCR and the PCR product was separated by an agarose gel electrophoresis to visually detect the band of c-Fos. Incidentally, the PCR primer (Sigma Genosys) for c-Fos was independently designed as the following sequences [c-Fos (178 bp): 5'-gcttcccttgatctgactgg-3' 5'-atgatgctgggaacag-gaag-3']. An example of the above test result is shown in FIG. 5.

Pharmacological Test 5: Effect to CREB Pathway

Figure 6:
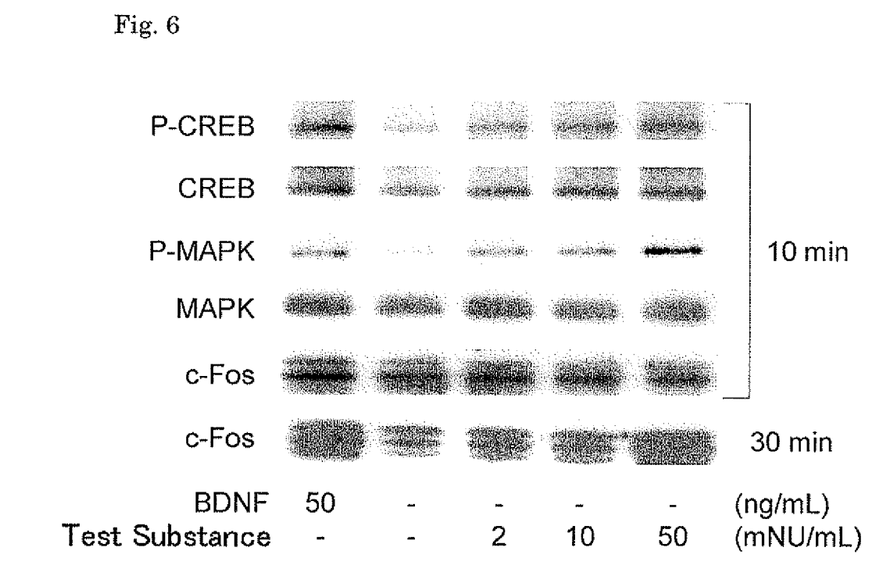
FIG. 6 is an electrophoretic drawing which shows the result where the expression of intracellular signaling molecules (in protein levels) in the CREB pathway was checked when SH-SY5Y cells were treated with the test substance or a human recombinant BDNF.

Intracellular signaling molecules were detected by an immuno-blotting method using each of various specific antibodies produced to CREB (MAB 5432; Millipore), phosphorylated CREB (P-CREB: Clone 10E9; Millipore), P42/44 MAP kinase (ERK1/2; Cell Signaling Technology), phosphorylated P42/44 MAP kinase (P-MAPK: Tyr202/Tyr204; Cell Signaling Technology) and c-Fos (Gene Tex). Thus, firstly, SH-SY5Y cells ($1 \times 10^6$ cells) were cultured for 6 hours in a serum-free DMEM medium and treated for 10 minutes or 30 minutes with human recombinant BDNF (50 pg/mL; Peprotech) or the test substance (0, 2, 10 or 50 mNU/mL). After that, the cells were scraped off using a cell scraper (BD Bioscience), immediately washed with ice-cooled PBS and subjected to cytolysis according to a method of Mutoh, et al. (*Proceedings of the National Academy of Sciences of the United States of America*, vol. 92, pages 5087 to 5091, 1995). The cytolyzed product was subjected to an SDS-PAGE electrophoresis of 4 to 20% gel (ePAGEL; Atto Chemicals) and blotted to a PDVF (polyvinylidene fluoride) membrane. After said membrane was subjected to a blocking for 1 hour using Tris buffer physiological saline (TBS; 20 mM Tris-HCl, pH 7.5, 0.15M NaCl) containing 3% fat-free milk and 0.1% Tween 20 (TBS-T), a reaction with the primary antibody and the HRP-labeled secondary antibody was conducted in TBS-T for one hour at room temperature. Immuno-reactive bands of CREB, phosphorylated CREB, P42/44 MAP kinase, phosphorylated P42/44 MAP kinase and c-Fos were visually detected by a detection system by means of electrochemical luminescence (ECL; GE Healthcare). An example of the above test result is shown in FIG. 6.

Figure 7:
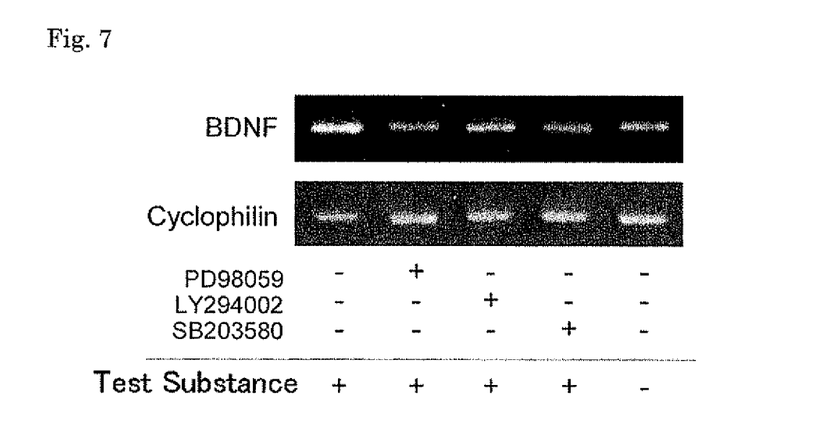
FIG. 7 is an electrophoretic drawing which shows the result where the influence of inhibitors to intracellular signaling molecules of CREB pathway on BDNF expression (in mRNA levels) was checked when SH-SY5 cells were treated with the test substance.

Pharmacological Test 6: Influence of Intracellular Signaling Inhibitors on BDNF Expression SH-SY5Y cells ($5 \times 10^5$ cells) were cultured for 24 hours in a serum-free DMEM medium in the presence of the test substance (10 mNU/mL). PD98059 (MEK inhibitor, 10 μM), LY 294002 (PI-3K inhibitor, 15 μM) or SB 203580 (p38 MAPK inhibitor, 0.5 μM) dissolved in a medium was added to a cultured product 30 minutes before completion of the cultivation. After that, the same as in the above Pharmacological Test 1, the extracted total RNA was subjected to a semi-quantitative RT-PCT, the PCR product was separated by agarose gel electrophoresis and the bands of BDNF and cyclophilin were visually detected. An example of the above test result is shown in FIG. 7.

Pharmacological Test 7: Amount of Intracellular cAMP

Figure 8:
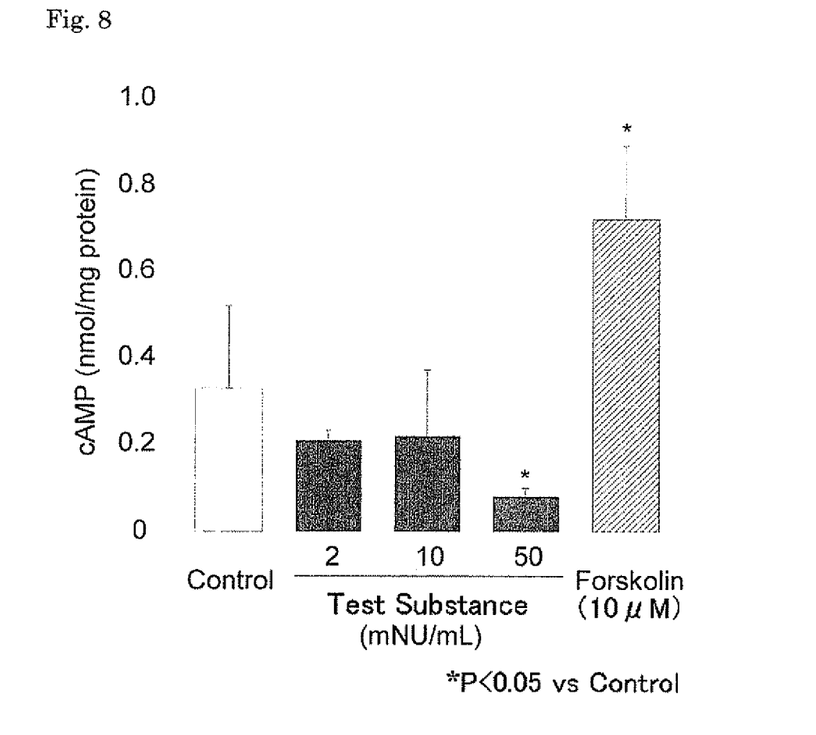
FIG. 8 is a graph which shows the result where the amount of intracellular cyclic AMP (cAMP) was checked when SH-SY5Y cells were treated with the test substance or phosphoryl choline.

SH-SY5Y cells were sown in 3.75×10$^5$ cells/well on a 24-well culture plate and treated in a serum-free DMEM medium for 30 minutes with the test substance (2, 10 or 50 mNU/mL) or with forskolin (10 μM; Sigma) as a positive control. Immediately after removing the supernatant fluid of the culture, cytolysis was conducted at 4° C. with 300 μL/well of 0.1M hydrochloric acid. The intracellular amount of cAMP in the cytolyzed product was directly measured by an ETA (enzyme immunoassay) kit (Cayman Chemicals) according to the direction for use of the manufacturer. Protein concentration was measured by a BCA protocol (Thermo Fisher Scientific) using a BSA standard solution (Thermo Fisher Scientific). The result is shown in terms of mean value of measurements for four times and standard deviation. An example of the above test result is shown in FIG. 8.

Pharmacological Test 8: Influence on TrkB Inhibition

Figure 9:
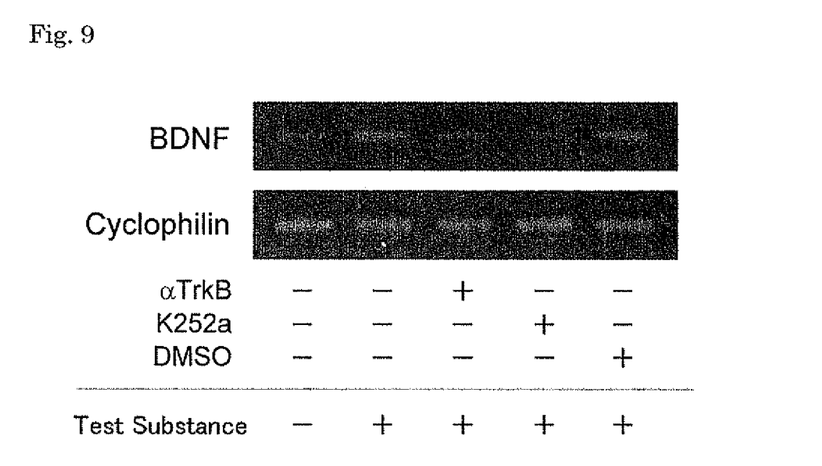
FIG. 9 is an electrophoretic drawing which shows the result where the influence of anti-TrkB antibody or tyrosine kinase inhibitor, etc. on the expression of BDNF, etc. was checked when SH-SY5Y cells were treated with the test substance.

SH-SY5Y cells (5×10$^5$ cells) were cultured with the test substance (10 mNU/mL) for 24 hours in a serum-free DMEM medium. K252a (tyrosine kinase inhibitor, 500 nM) or rabbit IgG of human TrkB-specific antibody (αTrkB, 20 μg/mL) was added to the cultured product 30 minutes before completion of the cultivation. After that, the same as in the above Pharmacological Test 1, the extracted total RNA was subjected to a semi-quantitative RT-PCR, the PCR product was separated by agarose electrophoresis and the bands of BDNF and cyclophilin A were visually detected. An example of the above test result is shown in FIG. 9.

Pharmacological Test 9: Internalization of TrkB

Density of the TrkB molecules on cell surfaces was measured by a partially improved method by Serres and Carney (*Brain Research*, vol. 1101, pages 36 to 42, 2006). Thus, firstly, SH-SY5Y cells were sown at 1×10$^5$/mL, cultured and treated with the test substance (2, 10 and 50 mU/mL) in a DMEM medium containing 1% FCS. In order to prevent the internalization of the receptor, the cells were washed for three times with ice-cooled PBS to which 0.1 mM calcium chloride and 1 mM magnesium chloride were added. After that, the molecules on the cell surfaces were biotinized at 4° C. for 30 minutes using 250 μg/mL of EZ-Link sulfo-LC-LC-NHS-biotin (Thermo Fisher Scientific) dissolved in PBS. In order to suppress the unreacted biotinizing reagent, washing with ice-cooled PBS containing 10 mM glycine was conducted and, after that, cytolysis was carried out with a minimum amount of a cytolyzing buffer (1% Nonidet P-40, 0.5% sodium deoxycholate and 0.1% SDS in PBS) containing a mixture of protease inhibitors (Sigma). Protein concentration was adjusted to 50 μg/mL using a cytolyzing buffer to prepare a sample.

Figure 10:
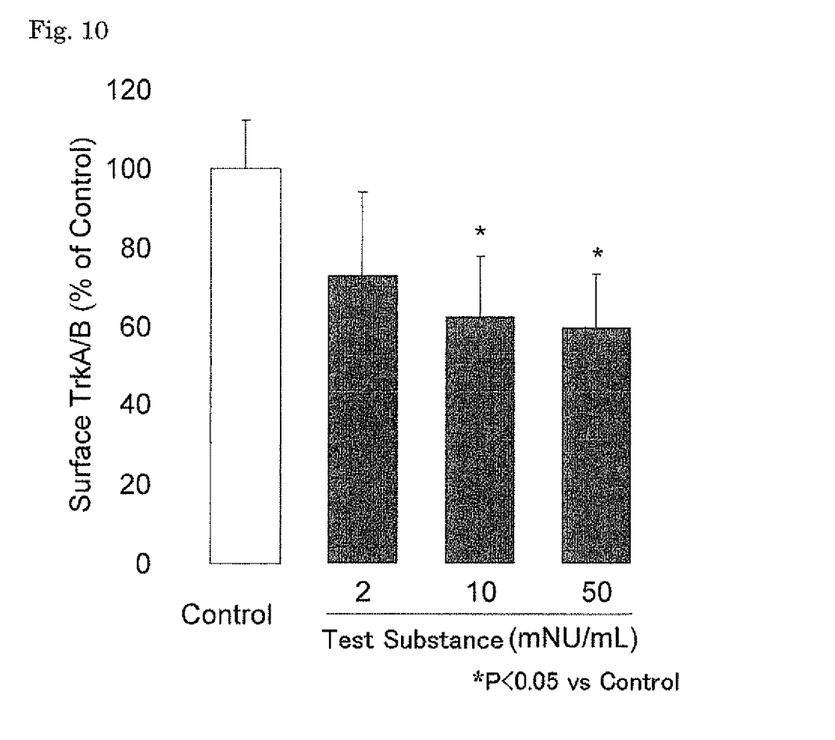
FIG. 10 is a graph which shows the result where the amount of TrkA/B on cell surfaces was checked when SH-SY5Y cells were treated with the test substance.

Five μg of a sample (100 μL) was cultured at room temperature for 2 hours on a plate where streptavidin was immobilized. After washing with PBS containing 0.2% of Tween 20 for three times, a rabbit anti-Trk antibody (100 μL; Clone C-14, Santa Cruz Biotechnology) diluted to 1:1,000 was added thereto followed by being allowed to stand for 1 hour. After washing, an anti-rabbit IgG labeled with HRP (1:1,000, 100 μL: AP132P, Chemicon International) was added followed by being allowed to stand for 1 hour and then an enzymatic reaction with TMS One Substrate (100 μL; Promega) was carried out. The reaction was stopped by addition of 0.1N hydrochloric acid and the bound specific antibody was quantified by measuring the absorbance at 450 nm (Benchmark microplate reader). The result is shown in terms of mean value of n=3 and standard error and expressed in terms of percentage to the control. An example of the above test result is shown in FIG. 10.

Results of Pharmacological Tests (1) Enhancement of BDNF Expression in SH-SY5Y Cells by the Test Substance From the result of the Pharmacological Test 1 (FIG. 1) it was confirmed that BDNF expression was enhanced in mRNA levels with elapse of time when the SH-SY5Y cells were treated with the test substance. Intensity of induction of BDNF by the test substance after 24 hours from the cultivation was in the similar degree as that by retinoic acid which is a positive control.

From the results of the Pharmacological Test 2 (FIGS. 2 and 3), it was noted that the expressions of BDNF and neurotrophic factors (NGF and NT-3) other than BDNF were enhanced in mRNA levels when SH-SY5Y cells were treated with the test substance. However, the expression of TrkA and TrkB which are highly affinitive receptors of neurotrophic factor was not enhanced. Further, in those tests, it was likely that, in the enhancing effect for BDNF expression by the test substance, an optimum concentration (10 mNU/mL) is available.

Further, from the result of the Pharmacological Test 3 (FIG. 4), it was confirmed that an amount of BDNF in the cells (in protein levels) significantly increases by the treatment with the test substance in a concentration of 10 mNU/mL or higher. On the other hand, for a purpose of measuring the amount of free BDNF secreted to the outside of the cells, the amount of BDNF in the supernatant liquid of the culture was measured but it was not detected (limit for detection: 3.9 pg/mL). That will be due to the fact that the free BDNF is immediately incorporated into the cells by TrkB as reported by Balkowiec, et al. (*The Journal of Neuroscience*, vol. 20, pages 7417 to 7423, 2000) already.

(2) Mechanism of the Enhancement of the Expression of BDNF, etc. by the Test Substance It has been known that the expression of BDNF, etc. is controlled by Ras-MAP kinase cascade located at the down stream of the Trk receptors and by intracellular signaling cascade such as phosphorylation of CREB (*Current Opinion in Neurobiology*, vol. 11, pages 272 to 280, 2001). The same as in BDNF expression of, the expression of c-Foc which is a proto-oncogene rises by activation of CREB and, from the result of the Pharmacological Test 4 (FIG. 5), it was confirmed that c-Fos expression was enhanced when SH-SY5Y cells were treated with the test substance.

Further, from the result of the Pharmacological Test 5 (FIG. 6), it was noted that, within 10 minutes from the treatment of SH-SY5Y cells with the test substance, phosphorylation of the 133rd serine residue in CREB and phosphorylation of p42/44MAP kinase (ERK1/2) which is an upstream modulator thereof were enhanced. Incidentally, it was also noted that the test substance enhanced the phosphorylation of ERK1/2 in the test system using PC12 cells or Schwann cells.

Similarly, BDNF which was given from outside of the cells also enhanced the phosphorylation of CREB and 42/44MAP kinase but, as shown in FIG. 1, the enhancing action of BDNF expression by the test substance was relatively time-consuming whereby it was likely that BDNF which was released to and enhanced in the outside of the cells did not indirectly cause the action of the test substance. Further, coinciding with this result, although each of PI3K, MEK1/2 and p38MAPK is a modulator (an intervening protein) of the CREB activation pathway started from TrkB receptor, it was noted from the result of the Pharmacological Test 6 (FIG. 7) that the enhancement of BDNF expression by the test substance was suppressed by an inhibitor to those modulators. Thus, the phosphorylation of Akt, ERK1/2 and CREB was inhibited by a PI3K inhibitor (LY294002), a MEK1/2 inhibitor (PD98059) and a p38MAPK inhibitor (SB203580), respectively. From the above, it was presumed that the target of the test substance is an upstream signaling cascade such as a PI3K/MAP kinase pathway or a Ras-MAP kinase cascade.

On the other hand, from the result of the Pharmacological Test 7 (FIG. 8), it was noted that the intracellular level of cAMP which is a modulator of the pathway being different from the above pathway in the CREB activation was not risen by the test substance but was significantly suppressed by the test substance particularly in a concentration of 50 mNU/mL. It was presumed from this result that the test substance activated a MAP kinase pathway instead of a cAMP-depending protein kinase pathway so that the transcription related to CREB was enhanced whereby the expression of BDNF and c-Fos was enhanced.

(3) Participation of TrkB in the Action of the Test Substance

It has been known already that the nerve action in the MAP kinase/CREB pathway is cooperatively adjusted via the activation of TrkB and, from the above pharmacological test, the participation of TrkB in the action of the test substance has now been made clear. To be more specific, it was confirmed from the result of the Pharmacological Test 8 (FIG. 9) that BDNF expression enhanced by the test substance was almost completely suppressed in the presence of a tyrosine kinase inhibitor K252a or Trk-specific antibody. Therefore, it was presumed that the test substance activated the endogenous tyrosine kinase using TrkB as a target directly and that, as a result of activation of MAP kinase/CREB pathway, BDNF expression was enhanced.

Further, from the result of the Pharmacological Test 9 (FIG. 10), it was noted that expression of TrkB on the cell surfaces significantly decreased upon the treatment by the test substance for 48 hours and it was presumed that the incorporation of TrkB into cells took place.

From the above, the followings may be induced as the present invention although they are mere exemplifications and the present invention is not limited thereto.

(1) A determining or evaluating method for an extract from inflamed tissues inoculated with vaccinia virus in which the action to the expression of neurotrophic factor in the cell is used as an indicator.

(2) The determining or evaluating method according to (1), wherein the action is an enhancing action for the expression.

(3) The determining or evaluating method according to (1) or (2), wherein the neurotrophic factor is BDNF.

(4) The determining or evaluating method according to (1) or (2), wherein the neurotrophic factor is NGF or NT-3.

(5) A determining or evaluating method for an extract from inflamed tissues inoculated with vaccinia virus in which the action to CREB in the cell is used as an indicator.

(6) The determining or evaluating method according to (5), wherein the action is an enhancing action for phosphorylation of CREB.

(7) The determining or evaluating method according to (6), wherein, in the enhancing action for phosphorylation of CREB, the production of c-Fos is measured and used as an indicator therefor.

(8) A determining or evaluating method for an extract from inflamed tissues inoculated with vaccinia virus in which the action to the activation of proteins intervening in the MAP kinase/CREB pathway of the cell is used as an indicator.

(9) The determining or evaluating method according to (8), wherein the action is an enhancing action for phosphorylation of the proteins.

(10) The determining or evaluating method according to (9), wherein the proteins intervening in the MAP kinase/CREB pathway is a protein in a MEK/ERK pathway.

(11) The determining or evaluating method according to (10), wherein the protein in the MEK/ERK pathway is Grb2, Sos, Ras, Raf, MEK1/2, ERK1/2 or Rsk.

(12) The determining or evaluating method according to (11), wherein the protein intervening in the MAP kinase/CREB pathway is a protein in a PI3K/Akt pathway.

(13) The determining or evaluating method according to (12), wherein the protein in the PI3K/Akt pathway is PI3K, Akt or P38MAPK.

(14) The determining or evaluating method according to any of (1) to (13), wherein the cell is a cultured cell.

(15) The determining or evaluating method according to (14), wherein the cell is SH-SY5Y cell.

(16) The determining or evaluating method according to any of (1) to (15), wherein the inflamed tissues are skin tissues.

(17) The determining or evaluating method according to any of (1) to (15), wherein the inflamed tissues are inflamed skin tissues of rabbits.

(18) An extract from inflamed tissues inoculated with vaccinia virus where its quality standards are guaranteed by the determining or evaluating method mentioned in any of (1) to (17).

(19) A method of guaranteeing the quality standards of the extract from inflamed tissues inoculated with vaccinia virus by conducting the determination or the evaluation mentioned in any of (1) to (17).

INDUSTRIAL APPLICABILITY

As will be apparent from the results of the above pharmacological tests where an extract from inflamed tissues inoculated with vaccinia virus is the test substance, it was noted that, when cultured cells are treated with the extract, an MAP kinase/CRED pathway is activated via activation of Trk whereupon expression of BDNF, c-Fos, etc. is enhanced.

Accordingly, when expression of BDNF, etc. or activation of protein participating therein is measured, it can be utilized, for example, for determining or evaluating the action of an extract from inflamed tissues inoculated with vaccinia virus or for guaranteeing the pharmaceutical effect of the extract.

Commercially available preparations of an extract from inflamed tissues inoculated with vaccinia virus are the pharmaceutical agents which have been widely used for many years due to excellent effect and high safety thereof. In an extract from inflamed tissues inoculated with vaccinia virus, the effective ingredient is not clear whereby its quality is guaranteed by a very troublesome method using SART stress mouse which is a chronic stress animal where the pain threshold is low as compared with the normal animal. On the contrary, the determining or evaluating method according to the present invention can carry out an in vitro test using cultured cells and, as compared with a determining method using specific morbid model animals, it is highly useful as a simple, convenient and quick determining or evaluating method for guaranteeing the quality of an extract from inflamed tissues inoculated with vaccinia virus.

The invention claimed is:

1. A method comprising:
    obtaining an extract from inflamed tissue inoculated with vaccinia virus;
    culturing a cell capable of expressing a neurotrophic factor comprising BDNF and/or NT-3 in a culture medium comprising the extract;
    measuring an intracellular expression level of the neurotrophic factor of the cell cultured in the culture medium comprising the extract; and
    comparing the intracellular expression level of the neurotrophic factor of the cultured cell to an intracellular expression level of the neurotrophic factor of a cell capable of expressing the neurotrophic factor cultured in a culture medium not comprising the extract.

2. The method according to claim 1, wherein the neurotrophic factor is BDNF.

3. The method according to claim 1, wherein the neurotrophic factor is NT-3.

4. The method according to claim 1, wherein the cell is SH-SY5Y cell.

5. The method according to claim 1, wherein the inflamed tissue is skin tissue.

6. The method according to claim 1, wherein the inflamed tissue is inflamed skin tissue of rabbits.

7. A method of guaranteeing the quality standards of the extract from inflamed tissues inoculated with vaccinia virus by conducting the method according to claim 1.

* * * * *